United States Patent
Zhang et al.

(10) Patent No.: US 11,732,234 B1
(45) Date of Patent: Aug. 22, 2023

(54) USE OF DIATOM IN RICE PLANTING AND CULTIVATION METHOD OF RICE IN SYMBIOSIS WITH DIATOM

(71) Applicants: Jiangxi Agricultural University, Nanchang (CN); Guangzhou Institute of Geochemistry, Chinese Academy of Sciences, Guangzhou (CN); Huazhong Agricultural University, Wuhan (CN)

(72) Inventors: Qin Zhang, Nanchang (CN); Dong Liu, Guangzhou (CN); Wenfeng Tan, Wuhan (CN); Guanjie Jiang, Nanchang (CN); Taihui Zheng, Nanchang (CN); Yupeng Yan, Nanchang (CN)

( * ) Notice: Subject to any disclaimer, the term of this patent is extended or adjusted under 35 U.S.C. 154(b) by 0 days.

(21) Appl. No.: 17/984,238

(22) Filed: Nov. 10, 2022

Related U.S. Application Data

(63) Continuation of application No. PCT/CN2022/118640, filed on Sep. 14, 2022.

(51) Int. Cl.
*C12N 1/12* (2006.01)
*A01G 22/22* (2018.01)

(52) U.S. Cl.
CPC ............. *C12N 1/12* (2013.01); *A01G 22/22* (2018.02)

(58) Field of Classification Search
CPC ..................................................... C12N 1/12
See application file for complete search history.

(56) References Cited

PUBLICATIONS

Jinsy, V.S. et al. Journal of Tropical Agriculture (2015), vol. 53, No. 1: pp. 1-7. (Year: 2015).*
Nayak, P.K. et al. (2018) vol. 91; pp. 359-375. (Year: 2018).*
Vijayan, D. and Ray, J.G., Journal of Plant Studies (2016) vol. 5, No. 2; pp. 1-15. (Year: 2016).*
The study summary of silicon nutrition about rice soil in our country, Feb. 29, 2008.
Biogeochemistry—Material cycling and soil processes, Mar. 31, 2017.
Microalgae function beyond your imagination! Enhance rice stress resistance, improve rice yield, Jul. 17, 2021.

* cited by examiner

*Primary Examiner* — Russell Kallis
(74) *Attorney, Agent, or Firm* — Swope & Yuy Ang IP Law Group

(57) ABSTRACT

The present application discloses the use of diatom in rice planting and a cultivation method of rice in symbiosis with diatom and relates to the technical field of rice planting. The use of diatom in rice planting is achieved by adding diatom to an irrigated paddy field and performing co-cultivation during rice planting. Co-cultivation of diatom and rice can effectively achieve the beneficial effects of increased yield/silicon, thicker straw, and increased lodging resistance in rice, and can reduce soil degradation, reduce the risk of heavy metal pollution and increase soil fertility.

5 Claims, 1 Drawing Sheet

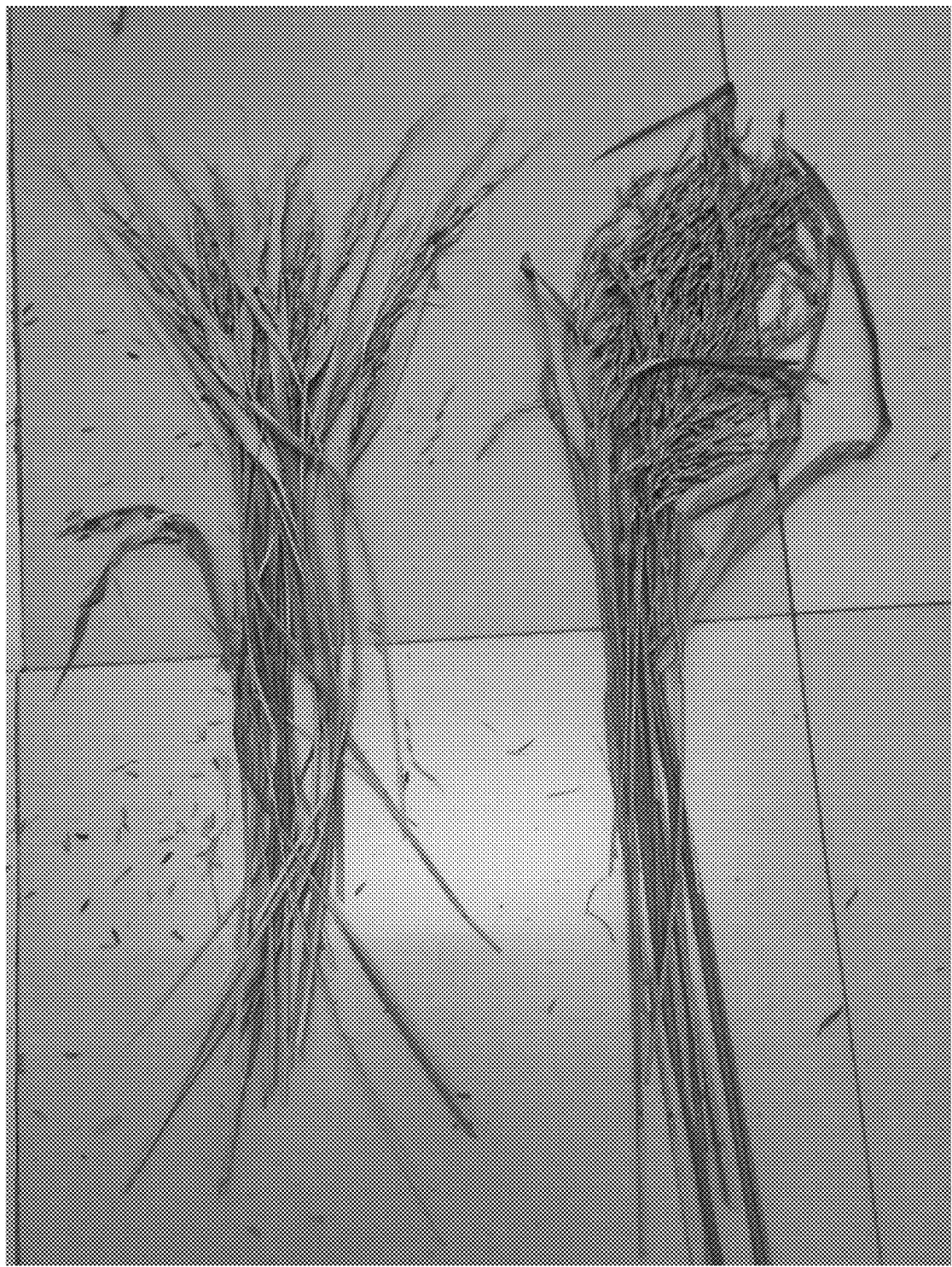

USE OF DIATOM IN RICE PLANTING AND CULTIVATION METHOD OF RICE IN SYMBIOSIS WITH DIATOM

The present application claims priority to Chinese patent application No. 202111112822.5, entitled "USE OF DIATOM IN RICE PLANTING AND CULTIVATION METHOD OF RICE IN SYMBIOSIS WITH DIATOM", filed on Sep. 18, 2021, the entirety of which is incorporated herein by reference.

TECHNICAL FIELD

The present application relates to the technical field of rice planting, in particular to the use of diatom in rice planting and a cultivation method of rice in symbiosis with diatom.

BACKGROUND

Rice is an important food crop with a long history of cultivation and consumption. Rice is an annual aquatic herb. Conventional rice planting usually includes the following steps: soil preparation, seedling raising, seedling transplanting, weeding and deinsectization, fertilization, irrigation and drainage, and harvesting. Among them, rice is more dependent on irrigation and drainage. Water irrigation should be enhanced after seedling transplanting, when forming panicles, as well as during the heading to flowering period. However, the current means for yield increase and silicon increase for rice are not effective.

In view of the above, the present application is proposed.

SUMMARY

The object of the present application is to provide use of diatom in rice planting and a cultivation method of rice in symbiosis with diatom.

The present application is achieved by the following:

In a first aspect, the present application provides use of diatom in rice planting.

In a second aspect, the present application provides use of diatom in the preparation of an additive for increasing yield and thickness or resisting lodging for rice.

In a third aspect, the present application provides a cultivation method of rice in symbiosis with diatom, comprising adding diatom to an irrigated paddy field and performing co-cultivation during rice planting.

In an alternative embodiment, the amount of viable cells of the diatom added to the irrigated paddy field is not less than $10^4$/L; and preferably, the amount of viable cells of the diatom added to the irrigated paddy field is between $10^4$-$10^5$/L.

In an alternative embodiment, the water level of the paddy field is maintained at 2.5-5.5 cm.

In an alternative embodiment, during rice planting, the growth cycle of rice includes a seedling stage, a regreening stage, a tillering stage, a panicle initiation stage, and a seed-setting stage, wherein the tillering stage, the panicle initiation stage and the seed-setting stage need irrigation treatment, and the diatom is added during at least one of the tillering stage, the panicle initiation stage and the seed-setting stage.

In an alternative embodiment, the soil in which the rice is grown is paddy soil.

In an alternative embodiment, the diatom is freshwater diatom; and preferably, the freshwater diatom comprises at least one of *Cyclotella meneghiniana* and *Nitzschia palea*.

In an alternative embodiment, the rice is selected from at least one of Lian jing 11, Xiang Zao Xian 45, Long Jing 39, Long Jing 43, Long Jing 31, Zhong Jia Zao 17, Sui Jing 14, Sui Jing 18, Nan Jing 9108, Huang Hua Zhan, Mei Xiang Zhan 2, 19 Xiang, Y Liang You 900, Quan You 822, Jing Liang You Hua Zhan, Long Liang You Hua Zhan, Jing Liang You 534 and Long Liang You 534.

In a fourth aspect, the present application provides the use of the cultivation method of rice in symbiosis with diatom of any one of the above embodiments in rice planting.

The present application has the following beneficial effects:

the use of diatom in rice planting provided in the present application can effectively achieve increased yield/silicon, thicker straw, and increased lodging resistance in rice by placing diatom in an irrigated paddy field and co-cultivating with rice. The growth of rice under conventional planting conditions reduces the pH value of the soil, resulting in gradual acidification of the soil. However, after co-cultivation with diatom using the cultivation method of the present application, alleviation of pH decrease can be effectively achieved since the diatom capture $HCO_3^-$ in water. Therefore, the co-cultivation of diatom and rice can slow down soil acidification, and the pH of the co-cultivation system does not change or increase compared with that before cultivation. Further, diatom forms its inherent organic components through photosynthesis and releases them into the soil after death, effectively increasing the content of organic matter in the soil. Therefore, the use of the cultivation method of rice in symbiosis with diatom provided by the present application can reduce soil degradation and increase soil fertility (organic matter content). It has great potential in increasing rice production and income.

BRIEF DESCRIPTION OF THE DRAWINGS

In order to illustrate the technical solutions of embodiments of the present application more clearly, the following briefly introduces the accompanying drawing that is required in the description of the embodiments. It is to be understood that the following drawing illustrates only certain embodiments of the present application and is therefore not to be considered limiting of scope. For those of ordinary skill in the art, other drawings can also be obtained from the drawing without any creative effort.

FIG. 1 shows the comparison of rice obtained from a cultivation system of rice alone (right) and a co-cultivation system of diatom-rice (left).

DETAILED DESCRIPTION

In order to make the objectives, technical solutions, and advantages of the embodiments of the present application clearer, the technical solutions in the embodiments of the present application will be described clearly and completely below. If specific conditions are not indicated in an embodiment, it is carried out according to conventional conditions or conditions suggested by the manufacturer. Reagents or instruments used without the manufacturer's indication are conventional products that can be purchased from the market.

The present application provides the use of diatom in rice planting, specifically comprising applying diatom during irrigation periods of rice planting. It is found through research that diatoms can promote the increase of rice yield, silicon content of straw, and lodging resistance.

The present application provides the use of diatom in the preparation of an additive for increasing yield and thickness or resisting lodging for rice. The additive may also include some conventional buffers, culture fluids, and the like.

The present application provides a cultivation method of rice in symbiosis with diatom, comprising adding diatom to an irrigated paddy field and performing co-cultivation during rice planting.

Diatoms are single-celled phytoplankton with chromatophores and are often connected by several or many individual cells into various populations. Diatoms can release oxygen through photosynthesis. At the same time, after diatoms die, their strong and porous shell, i.e. cell walls, will not decompose but will sink to the bottom of the water, and become diatomite after hundreds of millions of years of accumulation and geological changes. Diatomite can be mined and has many industrial uses. In the prior art, diatomite is used as a fertilizer for rice or raw material for seedling-raising substrates, but diatoms are rarely used directly.

In the present application, diatoms are innovatively put into irrigated paddy fields for cultivation to form a symbiotic system of rice-diatom, while in the prior art, many studies have been focused on the symbiosis of rice and other animals and plants, such as leech-rice symbiosis, rice-turtle symbiosis, rice-duck symbiosis, rice-prawn-rice symbiosis and rice-fish symbiosis. The symbiotic system of rice-diatom has not been studied at all, and even the direct use of diatoms in rice farming is rare.

In the present application, the normal growth of rice and diatoms can be ensured by adding diatoms to irrigated paddy fields and ensuring that the number of viable cells of diatoms is not less than $10^4$/L. Preferably, the amount of viable cells of diatoms added to the irrigated paddy field is between $10^4$-$10^5$/L. The water level of the paddy field is maintained at 2.5-5.5 cm.

Generally speaking, in freshwater aquaculture of diatoms, it is necessary to provide sufficient nutrients for the growth and division of diatoms, while in rice farming, if it is desirable to increase rice yield, increase the silicon content of straw, and enhance lodging resistance, it is necessary to provide adequate fertilizer or the like. However, the inventor found that diatoms can be directly put into the irrigated paddy fields without adding additional nutrients. The growth of diatoms will not only not affect the rice, but also can increase the yield of the rice, make the straw thicker and the silicon content higher, and enhance the lodging resistance. However, it should be noted that although diatoms can be cultured under near-neutral conditions or acidic conditions, diatoms are more adapted to near-neutral conditions. When the rice is flooded, the pH may be low. When the pH is lower than 6.0, the cultivation of diatoms can still be proceeding but the effect will be reduced. To this end, in the present application, an alkaline pH adjuster (for example, plant ash) can be added to the water body with lower pH to adjust the pH, but if the pH of the water body is around 6.5, it is not necessary to add the adjuster. Typically, for rice, the period from seed germination to the production of new rice seeds is called a reproductive period of rice, that is, a growth period. The growth period can be divided into a seedling stage, a regreening stage, a tillering stage, a panicle initiation stage (panicle differentiation stage), and a seed-setting stage.

The seedling stage includes a germination stage, an emergence stage, and a three-leaf stage.

The regreening stage refers to a buffer stage for rice to survive after the transplanting from a seedling field to a growth field.

The tillering stage includes an initial stage, a peak stage, an end stage (the highest tillering stage), and an effective tillering termination stage which is the key period that determines panicle number.

The panicle initiation stage (panicle differentiation stage) includes each stage of panicle differentiation, a jointing stage, and a booting stage when the flag leaf sheath is bulging in appearance.

The seed-setting stage includes heading to flowering stage, milk grain stage, dough grain stage, yellow ripening stage and full ripening stage.

Among them, the tillering stage, the panicle initiation stage, and the seed-setting stage need irrigation treatment. The diatoms are added during at least one of the tillering stage, the panicle initiation stage and the seed-setting stage. After planting, diatoms do not need to be picked up. When diatoms die naturally and are released into the soil, they can also increase the organic matter content of the soil.

In the present application, the soil for planting rice can be various paddy soils suitable for rice planting, especially soil with a reddish color is more suitable. Paddy soil has been in a flooded and anoxic state for a long time during planting rice. Thus the ferric oxide is reduced to ferrous oxide, which is easily soluble in water, thereby effectively promoting the growth and division of diatoms. Preferably, the soil in which rice is grown is paddy soil. Paddy soil refers to soil with unique cross-section characteristics due to the dual effects of human activities and natural soil-forming factors under the conditions of long-term flooding and rice cultivation, resulting in hydroponic maturation, alternation of oxidation and reduction, as well as leaching and deposition of substances. Due to the long-term flooded anoxic state, the ferric oxide in the soil is reduced to ferrous oxide, which is easily soluble in water and moves in the soil with water. When the soil is drained, or affected by rice roots (rice has aerenchyma tissues that provide oxygen to roots), the ferrous oxide is oxidized into ferric oxide precipitate, forming rust spots and rust lines. As a result, the lower soil layer is stickier and heavier. In the present application, paddy soil is used to plant rice. The paddy soil is rich in iron ions, which can effectively promote the growth and division of diatoms. The growth of rice can reduce the pH value of the soil, resulting in gradual acidification of the soil. However, after co-cultivation with diatom, alleviation of pH decrease can be effectively achieved since the diatom can capture $HCO_3^-$ in water during growth, such that soil acidification is alleviated. Further, diatom forms its own organic components through photosynthesis during growth and can release them into the soil after death, effectively increasing the content of organic matter in the soil. Furthermore, since diatoms have a good preference for Cd, the co-cultivation system can effectively reduce the concentration of free Cd and reduce the risk of Cd entering into rice grains.

In the present application, the diatom is freshwater diatom; preferably, the freshwater diatom comprises at least one of *Cyclotella meneghiniana* and *Nitzschia palea*. The *Nitzschia palea* in the present application belongs to benthic algae, which are not easy to be lost with water flow, and directly enter the soil after death, reducing the dissolution loss in water and the consumption by other organisms, thereby producing a better effect.

The above-mentioned cultivation method of rice in symbiosis with diatom has a wide range of applications and can be applied to a variety of rice. The rice includes, but is not limited to, at least one of Lian jing 11, Xiang Zao Xian 45, Long Jing 39, Long Jing 43, Long Jing 31, Zhong Jia Zao 17, Sui Jing 14, Sui Jing 18, Nan Jing 9108, Huang Hua Zhan, Mei Xiang Zhan 2, 19 Xiang, Y Liang You 900, Quan You 822, Jing Liang You Hua Zhan, Long Liang You Hua Zhan, Jing Liang You 534 and Long Liang You 534.

In addition, the present application also provides a cultivation system for rice in symbiosis with diatom, which includes irrigated paddy fields, rice planted in the paddy fields, and diatoms placed in the paddy fields. The cultivation system can be widely used in rice cultivation and provides a new idea for rice cultivation. The inventor found in research that placing diatom in an irrigated paddy field and co-cultivating with rice can effectively achieve increased yield/silicon, thicker straw, and increased lodging resistance in rice. The co-cultivation of diatom and rice can slow down soil acidification, and the pH of the co-cultivation system does not change or increase compared with that before cultivation. Furthermore, co-cultivation of diatoms and rice can also increase the content of organic matter in the soil, reduce the concentration of free Cd, and reduce the risk of Cd entering into rice grains, which has great potential in increasing rice production and income.

The features and performances of the present application will be further described in detail below in conjunction with examples.

Example 1

Rice was planted in paddy fields for conventional planting. When irrigating, *Cyclotella meneghiniana* with a viable cell amount of $10^4$/L was added and co-cultivated with rice while maintaining a water level of the paddy fields at 4.5-5.5 cm.

Example 2

Rice was planted in paddy fields for conventional planting. When irrigating, *Cyclotella meneghiniana* with a viable cell amount of $10^5$/L was added and co-cultivated with rice while maintaining a water level of the paddy fields at 4.5-5.5 cm.

Example 3

Rice was planted in paddy fields for conventional planting. When irrigating, *Nitzschia palea* with a viable cell amount of $10^5$/L was added and co-cultivated with rice while maintaining a water level of the paddy fields at 4.5-5.5 cm.

Example 4

Rice was planted in paddy fields for conventional planting. When irrigating, *Nitzschia palea* with a viable cell amount of $10^4$/L was added and co-cultivated with rice while maintaining a water level of the paddy fields at 4.5-5.5 cm.

Example 5

Rice was planted in paddy fields for conventional planting. When irrigating, *Cyclotella meneghiniana* with a viable cell amount of $10^4$/L was added and co-cultivated with rice while maintaining a water level of the paddy fields at 2.5-3.5 cm.

Comparative Example 1

Rice was planted in paddy fields for conventional planting.

The rice obtained in the above Examples 1-5 and Comparative Example 1 and the soil used for planting rice was tested and observed; the pH of the paddy field soil before planting was 4.74.

Wherein the method for detecting yield is a method of weighing after threshing and drying.

The method for detecting silicon content is an XRF test.

The method for detecting straw diameter is a Vernier caliper measurement.

The method for detecting flexural strength is a measurement using an Instron 3367 double-column desktop electronic testing machine.

The method for detecting organic matter is a potassium dichromate volumetric method.

| | Rice | | | | Soil condition of paddy field | |
|---|---|---|---|---|---|---|
| Example | Yield increase (%) | Silicon content of straw (% wt) | Straw diameter (mm) | Flexural strength (MPa) | pH after planting | Organic matter content (mg/g) |
| Example 1 | 17 ± 1 | 8.3 ± 0.1 | 4.1 ± 0.36 | 28.6 ± 6.5 | 4.92 | 25.1 |
| Example 2 | 21 ± 1 | 8.8 ± 0.1 | 4.3 ± 0.21 | 29.3 ± 3.7 | 4.93 | 26.0 |
| Example 3 | 27 ± 2 | 9.3 ± 0.2 | 4.5 ± 0.17 | 31.2 ± 6.9 | 4.98 | 26.9 |
| Example 4 | 20 ± 1 | 9.0 ± 0.1 | 4.1 ± 0.32 | 29.6 ± 4.8 | 4.86 | 24.9 |
| Example 5 | 13 ± 1 | 5.7 ± 0.1 | 3.7 ± 0.13 | 26.3 ± 5.5 | 4.73 | 23.1 |
| Comparative Example 1 | — | 4.2 ± 0.1 | 3.3 ± 0.52 | 20.1 ± 3.7 | 4.66 | 22.3 |

It can be seen from the above table that the diatom-paddy soil co-cultivation system greatly increased the yield of rice, the silicon content in the straw could be more than doubled, the diameter of the straw increased, and the flexural strength increased, and thus the lodging resistance was higher. In addition, the growth of diatoms in the paddy fields increased the content of organic matter in the paddy soils and inhibited the decrease in soil pH caused by rice cultivation.

In summary, the use of diatom in rice planting provided in the present application can effectively achieve increased yield/silicon, thicker straw (see FIG. 1), and increased lodging resistance in rice by placing diatom in an irrigated paddy field and co-cultivating with rice. The growth of rice under conventional planting conditions reduces the pH value of the soil, resulting in gradual acidification of the soil. However, after co-cultivation with diatom using the cultivation method of the present application, alleviation of pH decrease can be effectively achieved since the diatom capture $HCO_3^-$ in water. Therefore, the co-cultivation of diatom and rice can slow down soil acidification, and the pH of the co-cultivation system does not change or increase compared with that before cultivation. Further, diatom forms its own organic components through photosynthesis and releases them into the soil after death, effectively increasing the content of organic matter in the soil. Therefore, the use of the cultivation method of rice in symbiosis with diatom provided by the present application can reduce soil degradation, reduce the risk of heavy metal pollution and increase soil fertility (organic matter content). It has great potential in increasing rice production and income.

The above descriptions are only preferred embodiments of the present application and are not intended to limit the present application. For those skilled in the art, the present application may have various modifications and changes. Any modification, equivalent replacement, improvement, etc. made within the spirit and principle of the present application shall be included within the protection scope of the present application.

What is claimed is:

1. A cultivation method of rice in symbiosis with diatom, comprising adding diatom to an irrigated paddy field and performing co-cultivation during rice planting, wherein during rice planting, the growth cycle of rice includes a seedling stage, a regreening stage, a tillering stage, a panicle initiation stage and a seed-setting stage, the tillering stage, the panicle initiation stage and the seed-setting stage need irrigation treatment, the diatom is added during at least one of the tillering stage, the panicle initiation stage and the seed-setting stage, and the soil in which the rice is grown is paddy soil; and wherein the amount of viable cells of the diatom added to the irrigated paddy field is between $10^4$-$10^5$/L.

2. The method according to claim 1, wherein the water level of the paddy field is maintained at 2.5-5.5 cm.

3. The method according to claim 1, wherein the diatom is freshwater diatom.

4. The method according to claim 1, wherein the rice is selected from at least one of Lian jing 11, Xiang Zao Xian 45, Long Jing 39, Long Jing 43, Long Jing 31, Zhong Jia Zao 17, Sui Jing 14, Sui Jing 18, Nan Jing 9108, Huang Hua Zhan, Mei Xiang Zhan 2, 19 Xiang, Y Liang You 900, Quan You 822, Jing Liang You Hua Zhan, Long Liang You Hua Zhan, Jing Liang You 534 and Long Liang You 534.

5. The method according to claim 3, wherein the freshwater diatom comprises at least one of *Cyclotella meneghiniana* and *Nitzschia palea*.

* * * * *